(12) United States Patent
Urick et al.

(10) Patent No.: US 6,676,590 B1
(45) Date of Patent: Jan. 13, 2004

(54) CATHETER SYSTEM HAVING TUBULAR RADIATION SOURCE

(75) Inventors: Michael J. Urick, Rogers; Timothy G. J. Ehr, Elk River; Roger N. Hastings, Maple Grove, all of MN (US)

(73) Assignee: SciMed Life Systems, Inc., Maple Grove, MN (US)

(*) Notice: Subject to any disclaimer, the term of this patent is extended or adjusted under 35 U.S.C. 154(b) by 0 days.

(21) Appl. No.: 08/984,490

(22) Filed: Dec. 8, 1997

Related U.S. Application Data (63) Continuation-in-part of application No. 08/812,757, filed on Mar. 6, 1997, now Pat. No. 6,110,097.

(51) Int. Cl.⁷ .................................... A61N 5/00
(52) U.S. Cl. ................................................ 600/3
(58) Field of Search .................................. 600/1–8

(56) References Cited

U.S. PATENT DOCUMENTS

| | | | |
|---|---|---|---|
| 2,546,761 A | 3/1951 | Loftus | 128/1.2 |
| 2,862,108 A | 11/1958 | Meilink | 250/106 |
| 2,955,208 A | 10/1960 | Stevens | 250/108 |
| 3,060,924 A | 10/1962 | Rush | 128/1.2 |
| 3,147,383 A | 9/1964 | Prest | 250/108 |
| 3,324,847 A | 6/1967 | Zoumboulis | 128/1.2 |
| 3,505,991 A | 4/1970 | Hellerstein et al. | 128/1.1 |
| 3,643,096 A | 2/1972 | Jeffries, Jr. et al. | 250/108 R |
| 3,669,093 A | 6/1972 | Sauerwein et al. | 128/1.1 |
| 3,674,006 A * | 7/1972 | Holmer | 128/1.2 |
| 3,750,653 A | 8/1973 | Simon | 128/1.2 |
| 3,811,426 A | 5/1974 | Culver et al. | 128/1.2 |
| 3,861,380 A | 1/1975 | Chassagne et al. | 128/1.2 |
| 3,866,050 A | 2/1975 | Whitfield | 250/497 |
| 3,927,325 A | 12/1975 | Hungate et al. | 250/435 |
| 4,096,862 A | 6/1978 | DeLuca | 128/348 |
| 4,220,864 A | 9/1980 | Sauerwein et al. | 250/497 |
| 4,225,790 A | 9/1980 | Parsons, Jr. et al. | 250/497 |
| 4,244,357 A | 1/1981 | Morrison | 128/1.2 |
| 4,281,252 A | 7/1981 | Parsons, Jr. et al. | 250/497 |
| 4,314,157 A | 2/1982 | Gaines | 250/497 |

(List continued on next page.)

FOREIGN PATENT DOCUMENTS

| | | |
|---|---|---|
| CA | 2166915 A | 8/1996 |
| DE | 9102312.2 | 8/1992 |
| DE | 195 26 680 A1 | 1/1997 |
| DE | 197 54 870 A1 | 8/1998 |
| DE | 197 24 233 C1 | 12/1998 |
| DE | 197 58 234 * | 7/1999 |
| DE | 198 07 727 * | 7/1999 |

(List continued on next page.)

OTHER PUBLICATIONS

Raloff, "Nuclear Medicine Gets Friendlier—Experimental Therapies Seek to Poison Just the Disease", *Science News*, vol. 152, Jul. 19, 1997, pp. 40–41.

(List continued on next page.)

*Primary Examiner*—John P. Lacyk
(74) *Attorney, Agent, or Firm*—Crompton, Seager & Tufte, LLC.

(57) ABSTRACT

A radiation source for inhibiting restenosis including a radiation delivery tube having a radioactive distal region, the tube being adapted to slide over a guide wire within a radiation delivery catheter. One tube has radioactive material incorporated into the tube wall material. Another tube has radioactive material secured to the tube surface. One radiation delivery balloon catheter includes a common inflation and radiation delivery lumen, the lumen being sealed distally and having a radiation source guide wire within the lumen. The lumen is sealed from contact with bodily fluids and is filled with inflation fluid during use. In use, the catheter balloon is advanced to a site to be treated, the balloon inflated, and the radioactive tube advanced over the radiation source guide wire within the lumen.

20 Claims, 6 Drawing Sheets

U.S. PATENT DOCUMENTS

| | | | | |
|---|---|---|---|---|
| 4,364,376 A | 12/1982 | Bigham | | 128/1.1 |
| 4,584,991 A | 4/1986 | Tokita et al. | | 128/1.1 |
| 4,588,395 A | 5/1986 | Lemelson | | 604/59 |
| 4,631,415 A | 12/1986 | Sauerwein et al. | | 250/497.1 |
| 4,702,228 A | 10/1987 | Russell, Jr. et al. | | 128/1.2 |
| 4,706,652 A | 11/1987 | Horowitz | | 128/1.2 |
| 4,763,642 A | 8/1988 | Horowitz | | 128/1.2 |
| 4,763,671 A | 8/1988 | Goffinet | | 128/786 |
| 4,782,834 A | 11/1988 | Maguire et al. | | 128/344 |
| 4,784,116 A | 11/1988 | Russell, Jr. et al. | | 128/1.2 |
| 4,799,479 A | 1/1989 | Spears | | 128/303.1 |
| 4,815,449 A | 3/1989 | Horowitz | | 600/7 |
| 4,819,618 A | 4/1989 | Liprie | | 600/7 |
| 4,851,694 A | 7/1989 | Rague et al. | | 250/497.1 |
| 4,861,520 A | 8/1989 | van't Hooft et al. | | 252/644 |
| 4,881,937 A | 11/1989 | van't Hooft et al. | | 600/3 |
| 4,897,076 A | 1/1990 | Puthawala et al. | | 600/7 |
| 4,936,823 A | 6/1990 | Colvin et al. | | 600/7 |
| 4,963,128 A | 10/1990 | Daniel et al. | | 600/7 |
| 4,969,863 A | 11/1990 | van't Hooft et al. | | 600/3 |
| 4,976,266 A | 12/1990 | Huffman et al. | | 128/659 |
| 4,976,680 A | 12/1990 | Hayman et al. | | 600/7 |
| 4,976,690 A | 12/1990 | Solar et al. | | 604/96 |
| 5,030,194 A | 7/1991 | Van't Hooft | | 600/3 |
| 5,032,113 A | 7/1991 | Burns | | 604/96 |
| 5,059,166 A | 10/1991 | Fischell et al. | | 600/3 |
| 5,084,001 A | 1/1992 | Van't Hooft et al. | | 600/3 |
| 5,084,002 A | 1/1992 | Liprie | | 600/7 |
| 5,092,834 A | 3/1992 | Bradshaw et al. | | 600/7 |
| 5,103,395 A | 4/1992 | Spako et al. | | 364/413.26 |
| 5,106,360 A | 4/1992 | Ishiwara et al. | | 600/2 |
| 5,120,973 A | 6/1992 | Rohe et al. | | 250/497.1 |
| 5,139,473 A | 8/1992 | Bradshaw et al. | | 600/3 |
| 5,141,487 A | 8/1992 | Liprie | | 600/7 |
| 5,147,282 A | 9/1992 | Kan | | 600/1 |
| 5,163,896 A | 11/1992 | Suthanthiran et al. | | 600/8 |
| 5,176,617 A | 1/1993 | Fischell et al. | | 600/3 |
| 5,183,455 A | 2/1993 | Hayman et al. | | 600/7 |
| 5,199,939 A | 4/1993 | Dake et al. | | 600/3 |
| 5,213,561 A | 5/1993 | Weinstein et al. | | 600/7 |
| 5,267,960 A | 12/1993 | Hayman et al. | | 604/106 |
| 5,282,781 A | 2/1994 | Liprie | | 600/3 |
| 5,302,168 A | 4/1994 | Hess | | 600/3 |
| 5,308,356 A | 5/1994 | Blackshear, Jr. et al. | | 606/194 |
| 5,344,383 A | 9/1994 | Liping | | 600/3 |
| 5,354,257 A | 10/1994 | Roubin et al. | | 600/7 |
| 5,370,685 A | 12/1994 | Stevens | | 623/2 |
| 5,391,139 A | 2/1995 | Edmundson | | 600/7 |
| 5,395,300 A | * 3/1995 | Liprie | | 600/3 |
| 5,405,309 A | 4/1995 | Carden, Jr. | | 600/3 |
| 5,409,015 A | 4/1995 | Palermo | | 128/772 |
| 5,411,466 A | 5/1995 | Hess | | 600/3 |
| 5,417,653 A | 5/1995 | Sahota et al. | | 604/20 |
| 5,425,720 A | 6/1995 | Rogalsky et al. | | 604/198 |
| 5,429,582 A | 7/1995 | Williams | | 600/2 |
| 5,484,384 A | 1/1996 | Fearnot | | 600/3 |
| 5,498,227 A | 3/1996 | Mawad | | 600/3 |
| 5,503,613 A | 4/1996 | Weinberger | | 600/3 |
| 5,503,614 A | 4/1996 | Liprie | | 600/7 |
| 5,532,122 A | 7/1996 | Drukier | | 435/5 |
| 5,538,494 A | 7/1996 | Matsuda | | 600/1 |
| 5,540,659 A | 7/1996 | Teirstein | | 604/104 |
| 5,545,132 A | 8/1996 | Fagan et al. | | 604/96 |
| 5,556,389 A | 9/1996 | Liprie | | 604/264 |
| 5,575,749 A | 11/1996 | Liprie | | 600/3 |
| 5,605,530 A | 2/1997 | Fischell et al. | | 600/3 |
| 5,611,767 A | 3/1997 | Williams | | 600/2 |
| 5,616,114 A | 4/1997 | Thornton et al. | | 600/3 |
| 5,618,266 A | 4/1997 | Liprie | | 604/21 |
| 5,624,372 A | 4/1997 | Liprie | | 600/3 |
| 5,643,171 A | 7/1997 | Bradshaw et al. | | 600/1 |
| 5,649,924 A | 7/1997 | Everett et al. | | 606/15 |
| 5,653,683 A | 8/1997 | D'Andrea | | 604/21 |
| 5,662,580 A | 9/1997 | Bradshaw et al. | | 600/3 |
| 5,674,177 A | 10/1997 | Hehrlein et al. | | 600/3 |
| 5,683,345 A | 11/1997 | Waksman et al. | | 600/3 |
| 5,688,220 A | 11/1997 | Verin et al. | | 600/1 |
| 5,707,332 A | 1/1998 | Weinberger | | 600/3 |
| 5,713,828 A | * 2/1998 | Coniglione | | 600/7 |
| 5,720,717 A | 2/1998 | D'Andrea | | 604/21 |
| 5,722,984 A | 3/1998 | Fischell et al. | | 606/198 |
| 5,728,042 A | 3/1998 | Schwager | | 600/3 |
| 5,728,065 A | 3/1998 | Follmer et al. | | 604/96 |
| 5,730,698 A | 3/1998 | Fischell et al. | | 600/3 |
| 5,782,740 A | 7/1998 | Schneiderman | | 600/1 |
| 5,782,742 A | 7/1998 | Crocker et al. | | 600/3 |
| 5,795,286 A | 8/1998 | Fischell et al. | | 600/3 |
| 5,797,948 A | 8/1998 | Dunham | | 606/194 |
| 5,800,333 A | 9/1998 | Liprie | | 600/3 |
| 5,803,895 A | 9/1998 | Kronholz et al. | | 600/3 |
| 5,807,231 A | 9/1998 | Liprie | | 600/3 |
| 5,816,259 A | 10/1998 | Rose | | 128/898 |
| 5,816,999 A | 10/1998 | Bischoff et al. | | 600/3 |
| 5,820,553 A | 10/1998 | Hughes | | 600/426 |
| 5,833,593 A | 11/1998 | Liprie | | 600/3 |
| 5,840,008 A | 11/1998 | Klein et al. | | 600/3 |
| 5,840,009 A | 11/1998 | Fischell et al. | | 600/3 |
| 5,840,064 A | 11/1998 | Liprie | | 604/96 |
| 5,843,163 A | 12/1998 | Wall | | 623/1 |
| 5,851,171 A | 12/1998 | Gasson | | 600/3 |
| 5,851,172 A | 12/1998 | Bueche et al. | | 600/7 |
| 5,855,546 A | 1/1999 | Hastings et al. | | 600/3 |
| 5,857,956 A | 1/1999 | Liprie | | 600/7 |
| 5,863,284 A | 1/1999 | Klein | | 600/3 |
| 5,863,285 A | 1/1999 | Coletti | | 600/3 |
| 5,865,720 A | 2/1999 | Hastings et al. | | 600/3 |
| 5,871,436 A | 2/1999 | Eury | | 600/3 |
| 5,871,437 A | 2/1999 | Alt | | 600/3 |
| 5,873,811 A | 2/1999 | Wang et al. | | 600/5 |
| 5,879,282 A | 3/1999 | Fischell et al. | | 600/3 |
| 5,882,290 A | 3/1999 | Kume | | 600/3 |
| 5,882,291 A | 3/1999 | Bradshaw et al. | | 600/3 |
| 5,891,091 A | 4/1999 | Teirstein | | 604/104 |
| 5,897,573 A | 4/1999 | Rosenthal et al. | | 606/224 |
| 5,899,882 A | 5/1999 | Waksman et al. | | 604/96 |
| 5,910,101 A | 6/1999 | Andrews et al. | | 600/3 |
| 5,957,829 A | * 9/1999 | Thornton | | 600/3 |
| 5,961,439 A | * 10/1999 | Chernomorsky et al. | | 600/4 |
| 5,967,966 A | * 10/1999 | Kronholz et al. | | 600/3 |
| 5,971,909 A | * 10/1999 | Bradshaw et al. | | 600/3 |
| 5,976,106 A | * 11/1999 | Verin et al. | | 604/96 |
| 5,997,462 A | * 12/1999 | Loffler | | 600/3 |
| 5,997,463 A | * 12/1999 | Cutrer | | 600/8 |
| 6,010,445 A | * 1/2000 | Armini et al. | | 600/3 |
| 6,013,019 A | * 1/2000 | Fischell et al. | | 600/3 |
| 6,013,020 A | * 1/2000 | Meloul et al. | | 600/7 |
| 6,024,690 A | * 2/2000 | Lee et al. | | 600/3 |
| 6,030,333 A | * 2/2000 | Sioshansi et al. | | 600/3 |
| 6,033,357 A | * 3/2000 | Ciezki et al. | | 600/3 |

FOREIGN PATENT DOCUMENTS

| | | | |
|---|---|---|---|
| DE | 198 25 563 | * | 12/1999 |
| DE | 198 25 999 | * | 12/1999 |
| DE | 198 26 000 | * | 12/1999 |
| DE | 198 29 447 | * | 1/2000 |
| EP | 0 497 495 A2 | | 8/1992 |
| EP | 0 514 913 A2 | | 11/1992 |
| EP | 0 593 136 A1 | | 4/1994 |
| EP | 0 433 011 B1 | | 7/1994 |
| EP | 0 633 041 A1 | | 1/1995 |
| EP | 0 686 342 A1 | | 12/1995 |

| | | |
|---|---|---|
| EP | 0 688 580 A1 | 12/1995 |
| EP | 0 696 906 B1 | 2/1996 |
| EP | 0 749 764 A1 | 12/1996 |
| EP | 0 754 472 A2 | 1/1997 |
| EP | 0 754 473 A2 | 1/1997 |
| EP | 0 778 051 A1 | 6/1997 |
| EP | 0 801 961 A2 | 10/1997 |
| EP | 0 810 004 | 12/1997 |
| EP | 0 813 894 A2 | 12/1997 |
| EP | 0 629 380 B1 | 7/1998 |
| EP | 0 865 803 | 9/1998 |
| EP | 0 904 798 | 3/1999 |
| EP | 0 904 799 | 3/1999 |
| JP | 10071210 | 3/1998 |
| WO | WO 86/03124 | 6/1986 |
| WO | WO 93/04735 | 3/1993 |
| WO | WO 94/25106 | 11/1994 |
| WO | WO 94/26205 | 11/1994 |
| WO | WO 95/07732 | 3/1995 |
| WO | WO 95/19807 | 7/1995 |
| WO | WO 95/26681 | 10/1995 |
| WO | WO 96/06654 | 3/1996 |
| WO | WO 96/10436 | 4/1996 |
| WO | WO 96/13303 | 5/1996 |
| WO | WO 96/14898 | 5/1996 |
| WO | WO 96/17654 | 6/1996 |
| WO | WO 96/22121 | 7/1996 |
| WO | WO 96/29943 | 10/1996 |
| WO | WO 96/40352 | 12/1996 |
| WO | WO 97/07740 | 3/1997 |
| WO | WO 97/09937 | 3/1997 |
| WO | WO 97/18012 | 5/1997 |
| WO | WO 97/19706 | 6/1997 |
| WO | WO 97/25102 | 7/1997 |
| WO | WO 97/25103 | 7/1997 |
| WO | WO 97/40889 | 11/1997 |
| WO | WO 98/01183 | 1/1998 |
| WO | WO 98/01184 | 1/1998 |
| WO | WO 98/01185 | 1/1998 |
| WO | WO 98/01186 | 1/1998 |
| WO | WO 98/11936 | 3/1998 |
| WO | WO 98/16151 | 4/1998 |
| WO | WO 98/20935 | 5/1998 |
| WO | WO 98/25674 | 6/1998 |
| WO | WO 98/29049 | 7/1998 |
| WO | WO 98/30273 | 7/1998 |
| WO | WO 98/34681 | 8/1998 |
| WO | WO 98/36788 | 8/1998 |
| WO | WO 98/36790 | 8/1998 |
| WO | WO 98/36796 | 8/1998 |
| WO | WO 98/39052 | 9/1998 |
| WO | WO 98/39062 | 9/1998 |
| WO | WO 98/39063 | 9/1998 |
| WO | WO 98/40032 | 9/1998 |
| WO | WO 98/46309 | 10/1998 |
| WO | WO 98/55179 | 12/1998 |
| WO | WO 98/57706 | 12/1998 |
| WO | WO 99/01179 | 1/1999 |
| WO | WO 99/02219 | 1/1999 |
| WO | WO 99/04706 | 2/1999 |
| WO | WO 99/04856 | 2/1999 |
| WO | WO 99/10045 | 3/1999 |
| WO | WO 99/49935 | 10/1999 |
| WO | WO 99/56825 | 11/1999 |
| WO | WO 99/56828 | 11/1999 |
| WO | WO 99/61107 | 12/1999 |
| WO | WO 99/62598 | 12/1999 |
| WO | WO 99/66979 | 12/1999 |
| WO | WO 00/03292 | 1/2000 |
| WO | WO 00/04838 | 2/2000 |
| WO | WO 00/04953 | 2/2000 |
| WO | WO 00/09212 | 2/2000 |

OTHER PUBLICATIONS

Fackelmann, "Harbinger of a Heart Attack—Does a Protein in the Blood Foretell Heart Trouble", *Science News*, vol. 151, Jun. 14, 1997, pp. 374–375.

"Aids and Cancer Cured by Hyper–Oxygenation", *Now What*, Issue No. 1, 1987, Waves Forest, Monterey, California.

Li et al., "Reactive Oxygen Species Induce Apoptosis of Vascular Smooth Muscle Cell", *FEBS Letters*, 404, 1997, pp. 249–252.

Kalli, "Oxygen Emulsion The Question of Free Radicals", Internet Address http://www.livelinks.com/sumeria/oxy/rad2.html, Aug. 1, 1997.

Barry, "Reactive Oxygen Species in Living System—Source: Biochemistry, and Role in Human Disease", Internet Address http://www.livelinks.com/sumeria/oxy/reactive-.html, Jul. 21, 1997 from *American Journal of Medicine*, vol. 91, No. 3C, Sep. 30, 1991, p. 14S(9).

Block, "Peroxygen Compounds, Chapter 9", *Disinfection, Sterilization, and Preservation*, Fourth Edition, Lea & Febiger, Philadelphia, Copyright 1991.

Moore, "Free Radial Generation by Thyroid Peroxidase and Its Effects on Cells in Vitro", PhD. Dissertation, Group in Endocrinology–University of California, Berkeley, California, Dec. 1990.

Tjho–Heslinga et al., "Results of Ruthenium Irradiation of Uveal Melanoma", *Radiotherapty and Oncology*, vol. 29, 1993, pp. 33–38.

Lommatzsch et al., "Radiation Effects on the Optic Nerve Observed After Brachytherapy of Choroidal Melanomas with 106Ru/106Rh Plaques", *Graefe's Arch. Clin. Expo. Ophthalmol.*, 1994, 232:482–487.

Alberti, Radiotherapy of Intraocular and Orbital Tumors, Springer–Verlag, Berlin, Copyright 1993, pp. 363–367 and 23–30.

FLEXMEDICS, Nitinol . . . The Material of Choice for Safer, More Effective Medical Procedures, 1989, three pages.

Sutherland, "Managing Cancer Through Synergy", Administrative Radiology Journal, Nov. 1996, pp. 21–27.

* cited by examiner

CATHETER SYSTEM HAVING TUBULAR RADIATION SOURCE

CROSS REFERENCES TO CO-PENDING APPLICATIONS

This application is a continuation-in-part of U.S. patent application Ser. No. 08/812,757, filed Mar. 6, 1997, now U.S. Pat. No. 6,110,097 entitled "Perfusion Balloon Catheter with Radioactive Source", the entire disclosure of which is incorporated herein by reference. The present application is also related to U.S. patent application Ser. No. 08/782,471, filed Jan. 10, 1997, entitled "Intravascular Radiation Delivery System", and to U.S. patent application Ser. No. 08/612,061, filed Mar. 7, 1996, now abandoned entitled "Perfusion Balloon Angioplasty Catheter", the entire disclosures of which are herein incorporated by reference.

FIELD OF THE INVENTION

The present application is related to medical devices and methods for inhibiting restenosis in blood vessels. Specifically, the present invention is related to intravascular catheters utilizing a tubular member having a distally disposed radiation source over a core wire and methods of their use.

BACKGROUND OF THE INVENTION

Intravascular diseases are commonly treated by relatively non-invasive techniques such as percutaneous transluminal angioplasty (PTA) and percutaneous transluminal coronary angioplasty (PTCA). These therapeutic techniques are well known in the art and typically involve use of a guide wire and a balloon catheter, possibly in combination with other intravascular devices. A typical balloon catheter has an elongate shaft with a balloon attached proximate to its distal end and a manifold attached to the proximal end. In use, the balloon catheter is advanced over the guide wire such that the balloon is positioned adjacent a restriction in a diseased vessel. The balloon is then inflated and the restriction in the vessel is opened.

Vascular restrictions that have been dilated do not always remain open. In approximately 30% of the cases, a restriction reappears over a period of months. The mechanism of this restenosis is not fully understood. The mechanism is believed to be different from the mechanism that caused the original stenosis. It is believed that rapid proliferation of vascular smooth muscle cells surrounding the dilated region may be involved. Restenosis may be in part a healing response to the dilation, including the formation of scar tissue.

Intravascular radiation, including thermal, light and radioactive radiation, has been proposed as a means to prevent or reduce the effects of restenosis. For example, U.S. Pat. No. 4,799,479 to Spears suggests that heating a dilated restriction may prevent gradual restenosis at the dilation site. In addition, U.S. Pat. No. 5,417,653 to Sahota et al. suggests that delivering relatively low energy light, following dilatation of a stenosis, may inhibit restenosis.

Delivery of radioactive radiation has been proposed as a means to prevent or reduce the effects of restenosis. Dake et al. suggest delivering radiation within the distal portion of a tubular catheter. Fischell, in the publication EPO 0 593 136 A1, suggests placing a thin wire having a radioactive tip near the site of vessel wall trauma for a limited time to prevent restenosis. Problems exist in attempting to provide uniform radiation exposure using a point or line source. Specifically, as the radiation varies inversely with the square of distance for a point source and inversely with distance for a line, a source laying off center near one vessel wall may significantly overexpose the nearby wall while underexposing the further away wall. This is especially critical for beta radiation which is absorbed by tissue and blood at a relatively short distance from the source.

Use of continuous centering balloons having a beta radiation source within has been suggested, but may allow the radiation source to "warp" when placed across curved vessel regions, allowing the balloon to bend but having the central radiation source lying in a straight line between the two ends.

What remains to be provided is an improved apparatus and method for delivering uniform radiation to vessel interiors to inhibit restenosis.

SUMMARY OF THE INVENTION

The present invention includes a radiation source which can be used to inhibit restenosis of blood vessels, the source having a tubular radioactive distal region adapted to slide over a radiation source guide wire or core wire. In all embodiments, the radiation source guide wire or core wire extends within a lumen, sealed on its distal end over substantially the entire length of a delivery catheter (at least distally to a point within an expandable balloon). The core wire further extends out the proximal end of the delivery catheter a sufficient distance or length to thread the tube or radiation source thereon. One radiation source includes a tubular body having a lumen the entire tube length, which can be used with a radiation source guide wire extending proximally out of the proximal end of a delivery catheter for at least the length of the tube. Another source includes a tubular body having a lumen the entire tube length but having a first guide wire port on its distal end and a second guide wire exit port a short distance proximal of the distal end, allowing the use of a shorter radiation source guide wire extending proximally from the proximal end of the delivery catheter to thread the tube thereon. Yet another source includes a short radioactive, tubular distal member disposed at the end of a shaft with the short distal tubular member having a distal and proximal opening for threading over the radiation source guide wire, again allowing the use of a radiation source guide wire which extends a short distance proximally out the proximal end of the delivery catheter to thread the tubular radiation source lumen thereon. The tubular body could also be of a two-piece construction with the short distal radiation portion detachable from a long proximal segment.

Still another radiation source features an elongate tubular body having a short distal radioactive portion and a lumen the entire tube length and having a longitudinal slot extending through the tube wall over a portion of the length of the tubular body. The slot extends from the proximal end of the tubular body, where it is open to the lumen at the proximal end, to a point proximate the radioactive portion. The slotted embodiment allows a radiation source guide wire to be threaded by extending the wire radially through the slot, holding the core wire position constant, while advancing the tube into the catheter and patient, thereby threading the entire tube while requiring the core wire to extend proximally from the proximal end of the delivery catheter a short distance about equal to the non-slotted length of the tubular body.

The tubular body can be formed of Nitinol. In a preferred embodiment, the elongate tubular body having the distally disposed radioactive source includes a plurality of cutouts or openings through the tubular wall in a distal portion thereof. The plurality of cutouts, holes or slots extend around the circumference of the tubular body and over a portion of the lengths thereof, wherein the cutouts are in a selected pattern separated by bridges of the material of the tubular body. The cutouts provide added flexibility in the distal portion of the tubular body which much navigate a more tortuous path to be positioned within the expandable balloon of the delivery catheter in a prior stenosed region. The cutouts, holes or slots may be distributed in any selected pattern to impart such increased flexibility. A preferred pattern includes a generally spiral or helical pattern of cutouts having bridges extending longitudinally between cutouts every 120 degrees. Radiation sources according to the present invention can have radioactive material incorporated into the tubular material or secured to the surface of the tubular body. In preferred embodiments, the tubular member is made from Nitinol with a metallic radiation source plated onto a portion of the surface thereof.

The present invention includes an inflatable balloon delivery catheter having a closed end radiation delivery lumen and a radiation source guide wire or core wire within the lumen. In one catheter, the radiation delivery lumen can serve as the inflation lumen. Another catheter includes an inflation lumen separate from the radiation source delivery lumen. Another preferred embodiment of delivery catheter includes a separate radiation source lumen and a separate inflation lumen in combination with a single operator exchange guide wire lumen which doubles as a passive perfusion lumen during radiation treatment.

The tubular radiation source and delivery catheter can be used in conjunction with a radiation shield or vault and a transfer tube. The vault can shield the radiation source when the source is outside of the patient's body. The transfer tube can be used to quickly transfer the radiation source from the vault into the delivery catheter. A preferred vault includes a path with multiple bends to shield the entrance and exit of the vault.

The tubular shape of the radiation source can provide a more even radiation exposure to vessel walls. In particular, due to the inverse square relationship between distance and radiation intensity, the tubular shape reduces the possibility for extreme under-exposure and over-exposure caused by a point or line radiation source becoming much closer to one side of a vessel than the other. The tube lumen, in combination with a core wire, provides a structure which can be used to advance the radiation source more safely. The distally sealed lumen through which the source travels prevents contamination with blood and is thus readily re-usable without sterilization. Further, the core wire constrains the movement of the tubular radiation source.

DETAILED DESCRIPTION OF THE PREFERRED EMBODIMENTS

Figure 1:
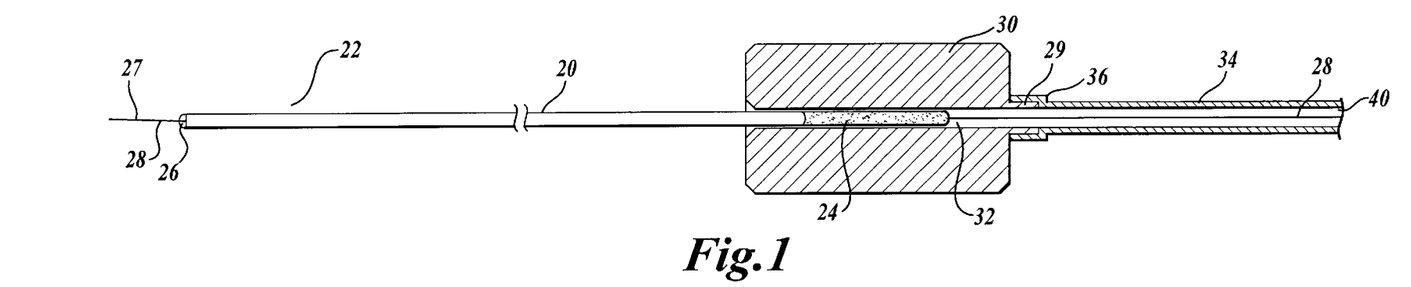
FIG. 1 is a fragmentary, longitudinal cross-sectional view of a radiation delivery tube having a radioactive distal region disposed over a radiation source guide wire and disposed within a radiation shielding vault coupled to a transfer tube.
Figure 2:
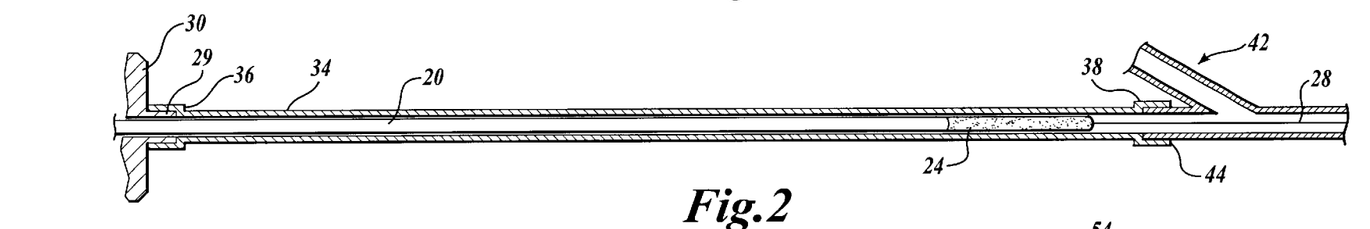
FIG. 2 is a fragmentary, longitudinal cross-sectional view of the vault, transfer tube, radiation delivery tube, and radiation source guide wire of FIG. 1 coupled to a radiation delivery catheter proximal end.
Figure 3:
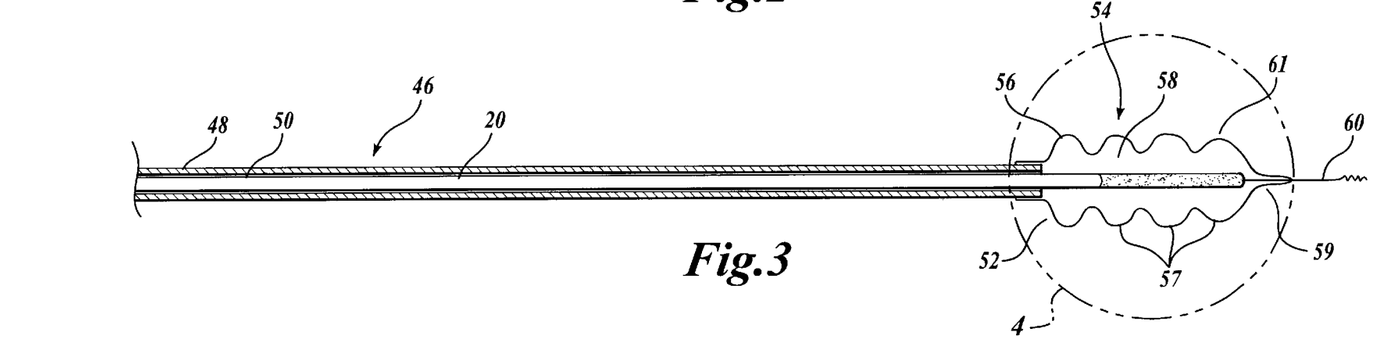
FIG. 3 is a fragmentary, longitudinal cross-sectional view of a fixed wire radiation delivery balloon catheter having the radioactive region of the radiation delivery tube of FIG. 1 inserted within the balloon.

Referring to FIGS. 1–3, an overall radiation delivery catheter system, including a radiation delivery tube 20, is schematically illustrated in various stages of deployment. FIG. 1 depicts the radiation delivery tube 20 as slidably mounted over a core wire or radiation source guide wire 28 while the distal portion or radioactive distal tubular region 24 remains shielded in a vault 30 prior to insertion into a catheter for use. FIG. 2 illustrates the radiation delivery tube 20 as extended distally from vault 30 into the lumen of a transfer tube 34, which in turn is connected to the proximal end 44 of a manifold 42 of a catheter 46. FIG. 3 depicts the radiation delivery tube 20 as fully extended distally into the catheter 46 with the distal radiation portion 24 of the radiation delivery tube 20 disposed within the balloon 56 for treatment of a stenotic region. It is noted that FIG. 3 depicts the catheter 46 as a fixed wire catheter having a single lumen. It is, however, recognized, as detailed herein, that the radiation delivery tube 20 of the present invention can be utilized in conjunction with other catheter designs which incorporate a lumen with a core wire extending therethrough and closed on the distal end to isolate the radiation delivery tube from the treatment site.

Now referring to FIG. 1 in more detail, FIG. 1 illustrates the radiation delivery tube or shaft 20 having a proximal region 22, a radioactive tubular distal region 24, and a lumen 26, disposed over a radiation source guide wire or core wire 28. In a preferred embodiment, proximal shaft region 22 has a lumen therethrough. In another embodiment, proximal shaft region 22 is solid, having no lumen. Radiation source guide wire 28 includes a proximal end 29, illustrated extending from radiation delivery tube proximal region 22. Radioactive distal region 24 is disposed within a channel 32 within a radiation shielding vault 30 coupled to a transfer tube 34. Transfer tube 34 includes a proximal coupling 36, a distal coupling 38 (illustrated in FIG. 2) and a lumen 40 therethrough. Radiation source guide wire 28 extends through radiation delivery tube 20, vault 30, and transfer tube 34. Radiation source guide wire 28 can originate distally in the distal end of a radiation delivery catheter 46 (illustrated in FIG. 3) and terminate in a proximal end 27.

A tubular member having a lumen extending through at least a distal portion thereof and a radiation source disposed on or in a distal segment thereof is the preferred device for delivery of radiation according to the present invention. Specifically, a tubular shaped source is preferred relative to a point or line source. The intensity of radiation delivered varies inversely with the square of the distance between the radiation source and target. A tubular source has radiation emitted from the tube walls surrounding the central axis of the tube, the radiation sources being disposed much closer to the target than would be sources positioned along the center of the tube. The tube shape is similarly shaped to most vessels being treated. The use of tubular sources allows advancing radiation sources over wires within existing catheters, not absolutely requiring the use of specialized devices to support delivery of a radiation source. As the radioactive material can be closer to the targeted vessel walls than the corresponding point or line source, the local strength of the sources can be less. This means that there is less chance of overexposing a vessel wall, should the radiation source be positioned closer to one side of a vessel than the other. In one embodiment, tube 20 has an inside diameter of about 0.014 inches to about 0.018 inches and an outside diameter of about 0.0175 inches to about 0.022 inches.

A preferred diameter for radiation source guide wire or core wire 28 is about 0.012 inch. Radiation source guide wire 28 can be formed from materials well known to those skilled in the art, such as stainless steel or Nitinol. In all embodiments of the invention illustrated, radiation source guide wire 28 is used to guide a radiation source slidably disposed thereover. Radiation source guide wire 28 terminates in catheter distal region and is contained in a lumen such that radiation delivery tube 20 is not in contact with bodily fluids. Contamination of the radiation source by bodily fluids is thus avoided. This allows for re-use of the radiation source in multiple patients.

Radiation delivery tube 20 can be formed from polymeric or metallic materials. Suitable polymers can include polyesters, polyamide or polyether block amides (PEBA). Suitable metals include stainless steel and Nitinol. Radiation delivery tube lumen 26 extends through the entire tube length in some embodiments. In other embodiments, tube 20 has a short lumen extending only through a distal tube region, having a proximal port in the distal region. This port allows radiation source guide wire proximal end 27 to be threaded through the short lumen portion, not requiring a radiation source guide wire extending proximally out of the proximal end of the delivery catheter at least a distance equal to the length of the radiation delivery tube. In embodiments having a lumen extending the entire length of tube 20, the radiation source wire must extend for at least this length from the proximal end of the catheter to allow for threading of the lumen without losing control of the wire.

Figures 4, 5, 6:
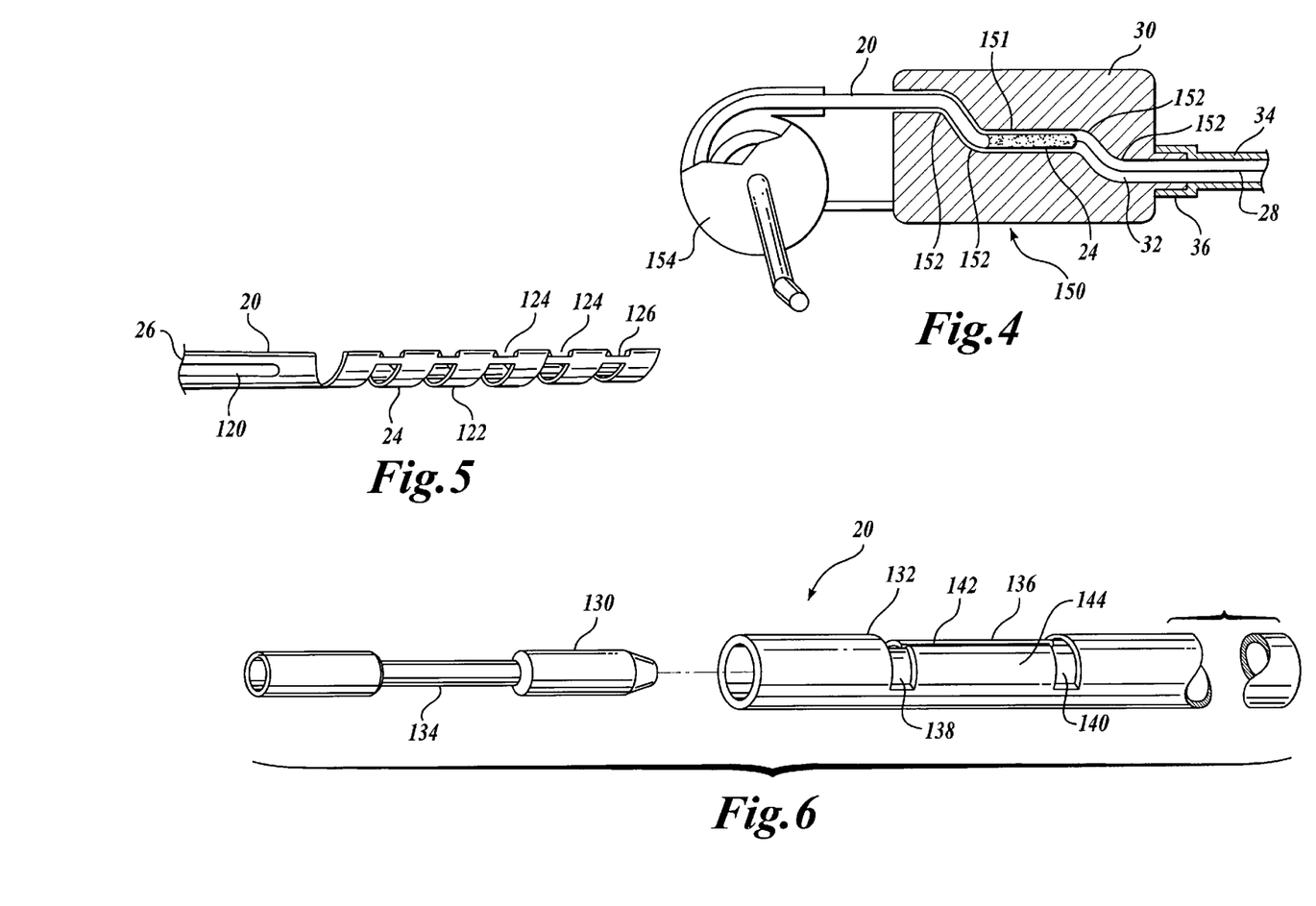
FIG. 4 is a schematic cross section of a preferred catheter management system including a vault having a tubular radiation source path therethrough including multiple bends to shield against radiation exposure in both a radial and longitudinal direction and a reel assembly which contains the non-radioactive portion of the tubular body.
FIG. 5 is a plan view of a preferred radioactive tubular body construction incorporating a guide wire slot extending from the proximal end of the tubular body to a point proximate the radioactive portion of the tubular body and also incorporating a plurality of cutouts to increase flexibility of the distal portion of the tubular body.
FIG. 6 schematically depicts a two-piece tubular radiation source which includes a detachable distal portion having the radioactive source thereon and a long proximal member for attachment thereto.

As depicted in FIG. 5, radiation delivery tube 20 can include a longitudinally extending slot 120 which extends from the proximal end of the radiation delivery tube 20 to a point proximate the radioactive tubular distal region 24. This "slotted tube" embodiment radiation delivery tube 20 has a lumen 26 extending the entire length of the tube 20 and a slot 120 through the tube wall into the lumen extending from the proximal end of the radiation delivery tube to a point proximate the distal portion of the radiation tube 20, with a short distal segment remaining unslotted. In this embodiment, the radiation source guide wire can be threaded through the lumen 26 of the short unslotted segment, extending transversely through the distalmost portion of the slot. As the radiation delivery tube is advanced distally, the radiation source guide wire or core wire fits radially through the slot into the lumen causing the entire wire to ultimately lie within the lumen when the delivery tube is fully advanced. In yet another embodiment, radiation delivery tube 20 includes a solid proximal radiation delivery shaft, with only the distal region having a lumen with proximal and distal openings to accept a wire.

As previously stated, the radiation delivery tube 20 can preferably be formed of Nitinol. As depicted in FIG. 5, the distal portion 122 of the radiation delivery tube 20 preferably includes a plurality of cutouts or openings 124 through the tubular wall in that distal portion. The plurality of cutouts, holes or slots extend around the circumference or a portion of the circumference of the radiation delivery tube in spaced arrangement over a portion of the length thereof. The cutouts are in a selected pattern separated by bridges 126 of the Nitinol material of the tubular member. These cutouts 124, in conjunction with the bridges 126, provide added flexibility in the distal portion of the radiation delivery tube 20. This assists in allowing the radiation delivery tube 20 to navigate the more tortuous path to the stenosed region. Although it is recognized that many patterns of cutouts, holes or slots may be utilized to impart the increased flexibility, a preferred pattern includes a generally spiral or helical pattern of cutouts having bridges extending longitudinally between cutouts every 120°.

Referring now to FIG. 6, an alternative two-piece embodiment of radiation delivery tube 20 is depicted. The two-piece embodiment includes a proximal member 130, which is releasably securable to a distal member 132. When attached together, the two members 130, 132 form the complete tubular radiation source 20, which can be utilized as previously described. In one preferred embodiment, as depicted in FIG. 6, the proximal member 130 includes a portion of reduced outside diameter 134. The distal member 132 includes a region 136, having a reduced diameter lumen. The reduced diameter lumen 136 illustrated in FIG. 6 is formed by cutting partial radial slots 138, 140 in spaced relation about equal to the length of the reduced diameter portion 134 of the proximal member 130. A slot 142 is cut longitudinally between the radial slots 138, 140. This forms two wings 144 from the wall material, which may be bent inwardly toward the center of the lumen, to form a portion of reduced diameter in the lumen. In this way, the reduced diameter portion 134 of proximal member 130 can be snap fit into the reduced lumen diameter portion of the distal member 132. The two-piece tubular member 20 design can be particularly useful with the radiation source disposed only on the distal member 132. In this way, the radiation containing member can be stored or shielded separately from the overall device.

As previously discussed with respect to FIG. 1, the radioactive portion of the radiation of the tube 20 is stored within a vault 30 prior to actual use in order to shield personnel from exposure. FIG. 4 illustrates a preferred design for a radiation tube 20 storage and handling device 150. First, the vault assembly 30 includes a lumen 32 which extends through the vault having a path which incorporates multiple bends or offsets 152. As depicted, the multiple bends or offsets provide shielding for personnel both in the radial and longitudinal directions when the radioactive distal portion 24 is disposed within the central cavity 151 of the vault 30. As also depicted in FIG. 4, the storage and delivery system can include a reel assembly 154 which is fixedly secured to the vault 30 proximal thereof. The reel assembly 154 can be utilized to manage the proximal or non-radioactive portion of the tubular radiation source 20. It can thus be used for storage, but also for advancing and retracting the tubular radiation source 20. Thus, the overall unit can be utilized to transfer or transport the assembly while always maintaining the radioactive distal portion 24 within the central cavity 151.

A preferred source of radiation to be used with the present invention is a ruthenium/rhenium source, in particular $Ru/Re_{106}$. This source is particularly useful in conjunction with a Nitinol radiation delivery tube as it can be plated onto the exterior surface of a distal portion of the radiation tube 20. An alternative source of radiation for all embodiments of the present invention is the radioactive compound Nickel-66. Nickel-66 decays with a half life of 2.28 days with only low energy beta emissions and no gamma emission into its daughter element Copper-66. Copper-66 then emits high energy beta radiation with a half life of 5.10 minutes and decays into the stabile element Zinc-66. This two-step decay has a particular advantage in use in the catheters of the present invention.

The Nickel-66 acts as a carrier for the high energy copper decay allowing for time to transport the source to the end user, and also allows for disposal of the device through ordinary means in about 23 days. A Copper-66 source alone would decay quickly and not be useful without the parent Nickel. Nickel is low cost and has desirable mechanical properties in its pure form and in alloys, such as a Nickel Titanium alloy.

Another preferred radiation source is Gadolinium-153. Gadolinium-153 is a composite gamma source which can provide low energy gammas to vessel intima layer while providing higher energy gammas to penetrate calcified plaques and reach the adventitia. Moderate shielding can be used with Gadolinium-153, allowing the treating physician to remain in the room with the patient during therapy. Another preferred source of radiation can include Yttrium-90, a high energy beta emitter.

The above mentioned sources and other sources could be incorporated into the radiation delivery tube. In one embodiment, radioactive materials are admixed with polymeric materials and extruded as part of the tube. In another embodiment, radioactive materials are adhesively secured to the tube distal region. In yet another embodiment, radioactive material is included in wire form and wound around the tube distal region. The length of the tube radioactive distal region can be sized to approximate the length of the stenosis to be treated.

Referring again to FIG. 2, distal coupling 29 on vault 30 is mated to proximal coupling 36 on transfer tube 34, and a distal coupling 38 on transfer tube 34 is mated to a proximal end 44 of a radiation delivery catheter 42. Radiation source guide wire 28 is illustrated extending from catheter 42. Transfer tube 34 serves to transfer radioactive tube region 24 from vault 30 into catheter 42. Transfer tube 34 can reduce the chance of damage to radiation delivery tube distal end 24 caused by entering catheter proximal end 44 while off-center. Transfer tube 34 can also speed the radiation advancement into the patient's body, thereby reducing the time that the radiation source is neither within vault 30 nor within the patient at the area to be treated. In one embodiment, transfer tube 34 is formed of plastic.

Referring again to FIG. 3, a fixed wire radiation delivery balloon catheter 46 is illustrated, having a tubular shaft 48 defining a lumen 50 within. Catheter 46 includes a distal region 52 and a distally disposed inflatable centering balloon 54. Balloon 54 includes a balloon envelope 56 which defines generally a balloon interior 58 and an exterior 61. Catheter 46 terminates in a distal end 59 which is sealed to prevent entry of bodily fluids into catheter lumen 50 and exit of inflation fluid from lumen 50. Balloon interior 58 is thus not in fluid communication with balloon exterior 61. In a preferred embodiment, a distal coil 60 forms the distalmost portion of catheter 46.

In a preferred embodiment, balloon 54 is a multi-waisted centering balloon having a plurality of lobes or segments 57 as illustrated in FIG. 3. Balloon segments 57 in one embodiment are formed from a series of balloon tubes adhesively secured together. In another embodiment, balloon segments 57 are formed by blow molding. In this embodiment, balloon segments 57 can be spaced about 2 to 5 millimeters apart. In yet another embodiment, balloon segments are formed by spirally winding at least one inflatable tube about the catheter longitudinal axis.

Balloon 54 is preferably multi-waisted to provide improved centering capabilities. When a balloon carrying a tube within lies in a curved vessel passage, the balloon may have an arcuate shape conforming to the vessel, while the tube lies along a straight line joining the balloon ends. The straight line shape can bring the tube into very close proximity to the inside wall of the vessel curve. This can result in radiation overexposure and underexposure for the inside and outside walls of the curve, respectively. Use of a multi-waisted balloon can force the radiation tube inside to conform to an arcuate shape through the balloon waist centers.

Figure 7:
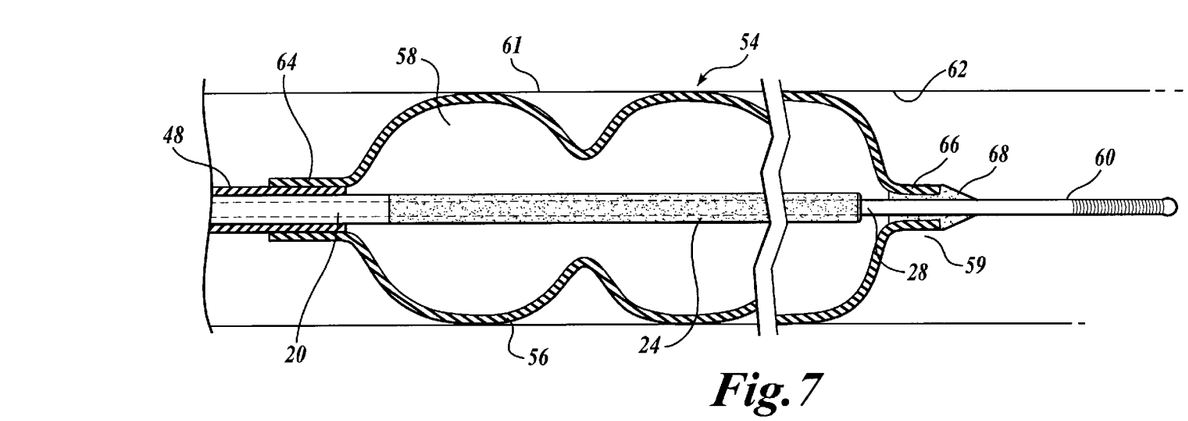
FIG. 7 is a fragmentary, longitudinal cross-sectional view of the balloon of FIG. 3.

Referring now to FIG. 7, balloon 54 is illustrated in more detail, disposed within vessel walls 62. Balloon envelope 56 includes a proximal waist 64 secured to tubular shaft 48 and a distal waist 66 secured over core wire 28. In one embodiment, balloon waists 64 and 66 are secured with adhesive or solvent bonding to underlying tube 48 and core wire 28, respectively. Radiation source guide wire 28 is secured to balloon distal end 59 in a fluid tight manner, such that distal fluid transfer in or out of balloon 54 is prevented. Radiation source guide wire 28 is fixed within balloon 54, such that wire 28 is not slidable relative to balloon 54. The annular space in lumen 50 between radiation source guide wire 28 and tubular shaft 48 defines an inflation lumen for inflating balloon envelope 56.

Figure 8:
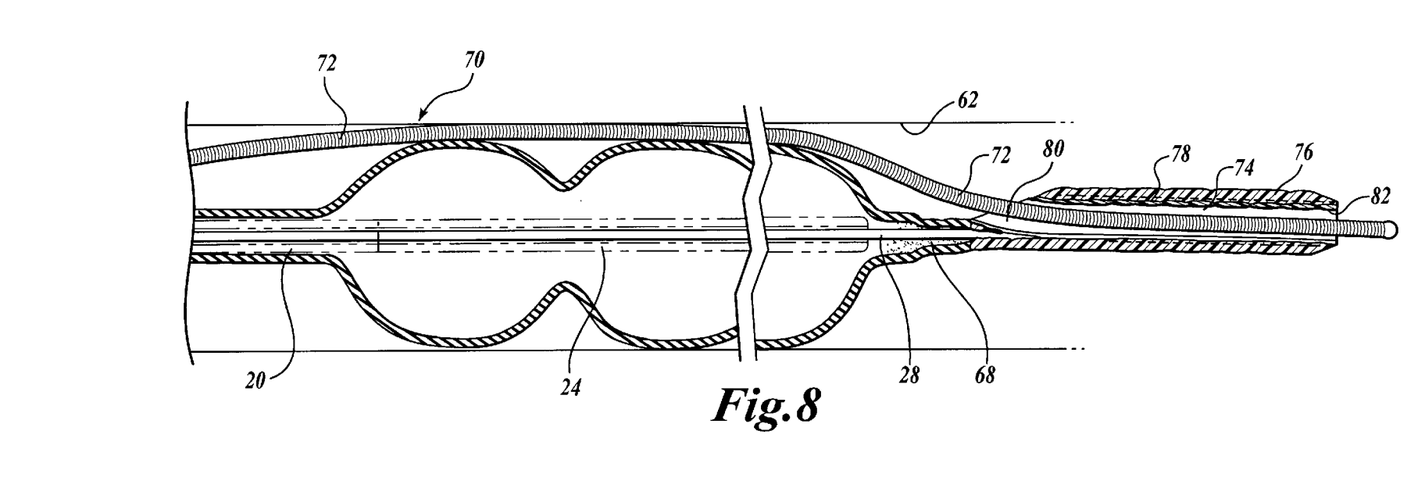
FIG. 8 is a fragmentary, longitudinal view of the balloon portion of a single operator exchange catheter embodiment having a catheter guide wire disposed within a distal guide wire lumen.

Referring now to FIG. 8, a single operator exchange radiation delivery catheter 70 is illustrated, having a catheter guide wire 72 disposed within a distal guide wire lumen 74. Radiation delivery catheter 70 is similar in many respects to fixed wire catheter 46, but having the ability to track over a guide wire. Catheter 70 includes a distal guide wire tube 76 having guide wire lumen 74, a proximal port 80, and a distal port 82. In a preferred embodiment, distal guide wire tube 76 includes a ribbon coil 78 embedded within to impart spring-like flexibility characteristics to the catheter distal tip. Coil 78 allows distal tube 76 to bend around tortuous curves without kinking yet return to a substantially straight tubular shape in straight passages.

Figure 9:
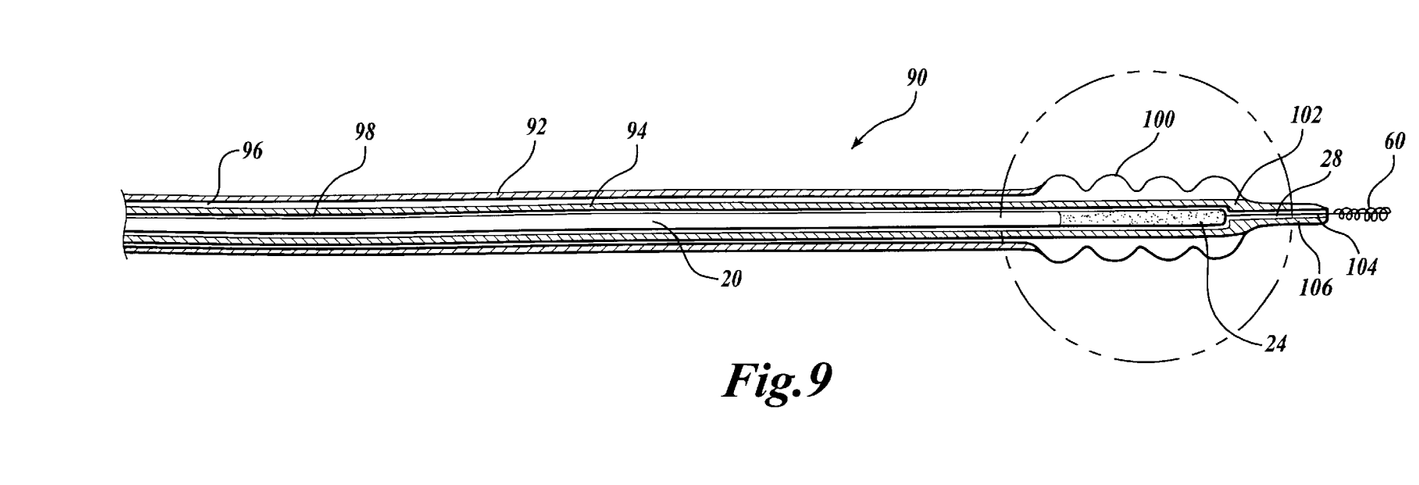
FIG. 9 is a fragmentary, longitudinal cross-sectional view of a radiation delivery balloon catheter having a radiation delivery tube disposed within an inner tube which is in turn disposed within an outer inflation tube.

Referring now to FIG. 9, a dual lumen embodiment of the present invention is illustrated in a catheter 90 having an outer tube 92 disposed about an inner tube 94. An inflation lumen 96 is defined in the annular space between outer tube 92 and inner tube 94. A radiation delivery lumen 98 is defined within inner tube 94 and is illustrated having radiation delivery tube 20 disposed within. Inflation lumen 96 is in fluid communication with an inflatable balloon 100. Inner tube 94 includes a distal region 102 extending through balloon 100 and sealing the interior of balloon 100 from radiation delivery lumen 98. In the embodiment illustrated, radiation source guide wire 28 is sealed with an adhesive 104 within a distal end 106 of catheter 90, terminating in distal coil 60.

In dual lumen catheter 90, radiation delivery tube 20 can remain dry during the procedure and no seal is required around the radiation source guide wire prior to inflation. In one embodiment, outer tube 92 has an outside diameter of about 0.045 inch and an inside diameter of about 0.040 inch. In one embodiment, inner tube 94 has an outside diameter of about 0.034 inch and an inside diameter of about 0.028 inch.

In use, a catheter such as catheters 42 and 46 illustrated in FIGS. 2 and 3 can be provided and inserted into a patient. Catheter 46 can be advanced until balloon 54 is in position across a treatment site having a lesion to be irradiated, leaving the catheter proximal end extending from the patient. A radiation delivery tube such as tube 20 of FIG. 1 can be provided, having radioactive distal region 24 shielded within vault 30. Transfer tube 34 can optionally be provided, interposed between, and coupled to, vault distal coupling 29 and catheter proximal end 44. Balloon 54 can be inflated with inflation fluid, dilating the stenosed vessel region. Radiation delivery tube radioactive region 24 can be rapidly advanced through transfer tube 34 and catheter lumen 50 to catheter distal region 52. After exposing the vessel treatment site for an appropriate period, radiation delivery tube 20 can be withdrawn into vault 30.

In embodiments having a common inflation and radiation delivery lumen, a seal can be provided around the radiation source guide wire near the proximal end of the catheter, to seal in inflation fluid. In embodiments having a separate inflation lumen, a seal is not required to contain inflation fluid and the radiation delivery tube can remain dry the entire procedure.

Figure 10:
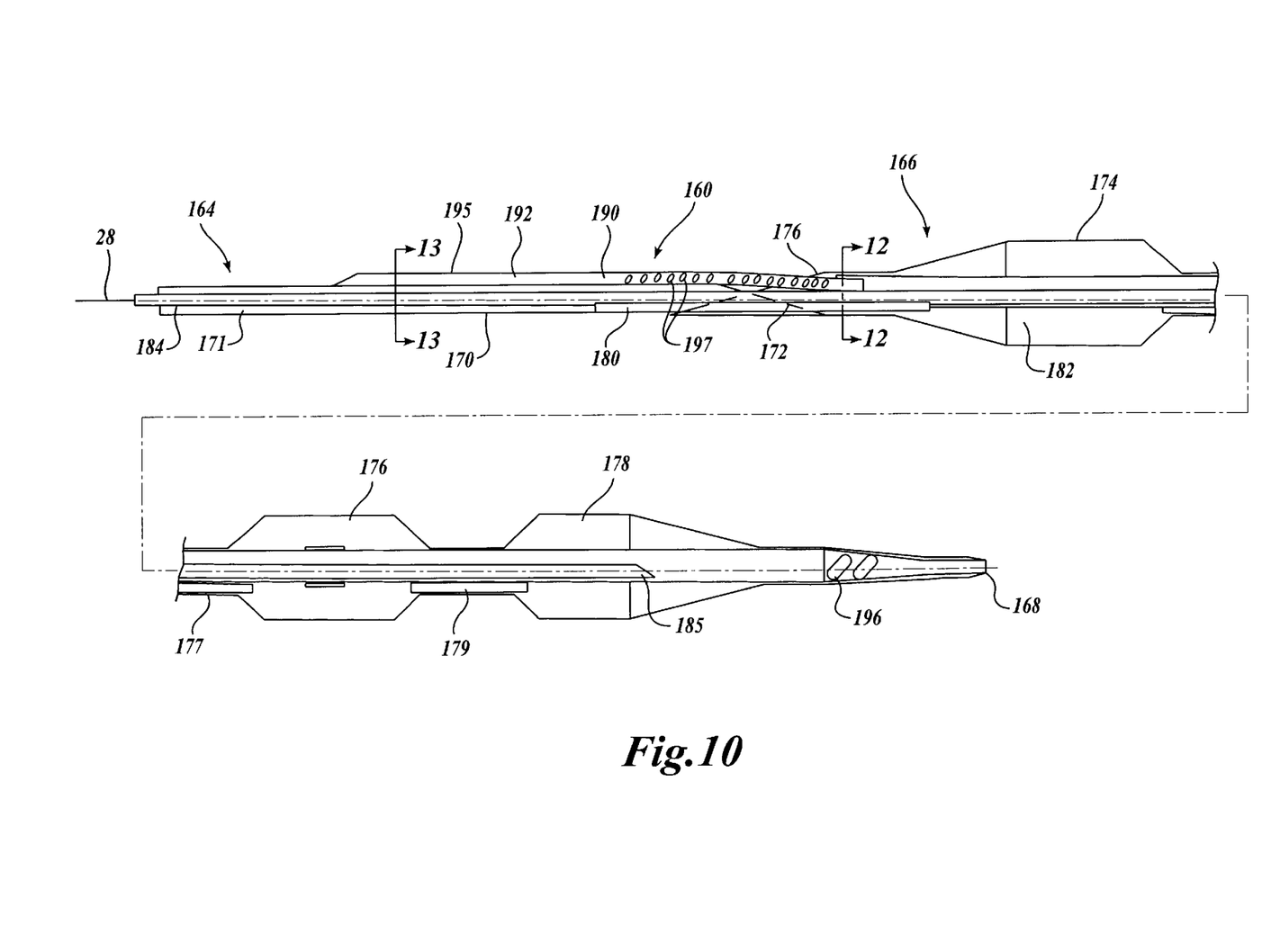
FIG. 10 is a fragmentary, longitudinal cross-sectional view of a delivery catheter incorporating a separate radiation delivery lumen, a separate inflation lumen and a combination perfusion lumen and single operator exchange guide wire lumen.
Figure 11:
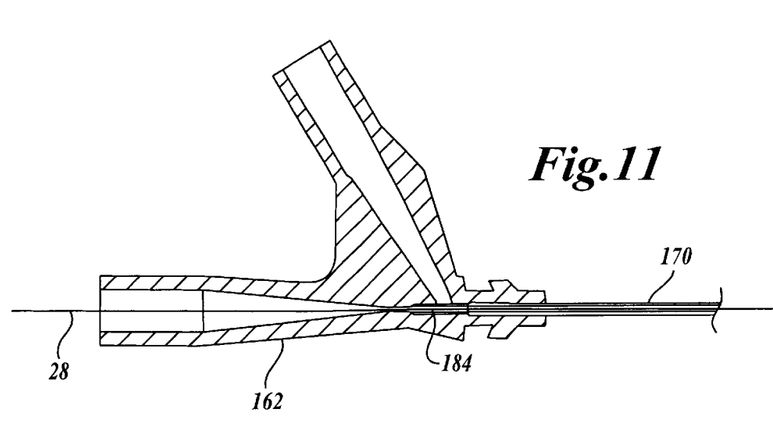
FIG. 11 is a fragmentary cross-sectional view of a manifold assembly for use in conjunction with the catheter of FIG. 10 depicting the core wire extending proximally from the proximal end of the manifold.

Referring now to FIG. 10, a preferred single operator exchange catheter design including a passive blood perfusion lumen and a radiation delivery tube lumen is illustrated. The figure shows a distal portion of catheter 160 connected proximally to a manifold 162 (the manifold is depicted in FIG. 11), having a proximal region 164, a distal region 166, and a distal end 168. The proximal region 164 of the catheter depicted in FIG. 10 includes a proximal shaft 170 which extends distally to a skived terminal end 172 which is proximal of the proximal balloon 174.

The proximal shaft portion 170 and skived portion 172 are affixed to a distal shaft portion 176 at the juncture as depicted. With the termination of the proximal tube 170, an inflation tubular member 180 extends from the distal end thereof and is in fluid communication with the lumen of the proximal tube 170. The distal end of the inflation tube 180 extends into the interior volume 182 of the balloon 174. Thus, inflation fluid may be transferred via the lumen 171 of proximal tube 170 into the balloon 174 through inflation tube 180. As depicted in FIG. 10, the balloon catheter of the present invention preferably includes multiple balloons to form multiple expandable segments. FIG. 10 depicts a proximal balloon 174, an intermediate balloon 176 and a distal balloon 178. Communication between the three balloons for inflation fluid is provided by an intermediate balloon inflation tube 177 and a distal balloon inflation tube 179 as depicted in FIG. 10. Alternatively, the inflation tubular member 180 can extend into all three balloons with an opening to the interior of each.

Also depicted in FIG. 10 is an inner tubular member 184 which extends from the proximal end of the catheter across the juncture between the proximal shaft 170 and distal shaft 176 into the interior of the balloon and terminates at a distal end 185 proximate the distal end of the distal balloon 178. This inner tubular member has a lumen extending therethrough which is closed at the distal end 185. The lumen has a core wire 28 extending therein. This lumen provides the conduit for insertion of and tracking of a radiation delivery tube 20 (not shown) as previously discussed herein.

Figure 12:
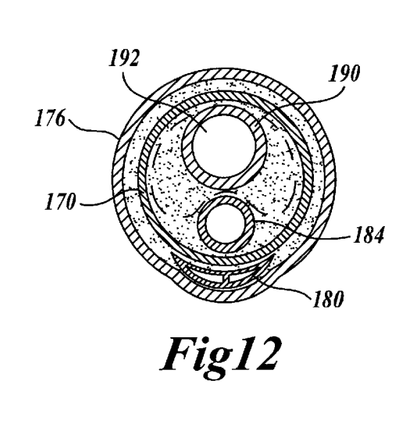
FIG. 12 is a cross section of the catheter of FIG. 10 at line 12—12.

Referring now also to FIG. 12, a cross-sectional view of catheter 160 at line 12—12, including distal region 166 is shown in more detail. Proximal shaft 170 is joined to distal shaft 176 with a crimped tube distal end 172. A guide wire tube 190 including a guide wire lumen 192, extends distally through the catheter, exiting catheter 160 at a distal port 168. Guide wire tube 190 extends through the balloons and is formed by distal shaft 176. A guide wire lumen proximal extension 195 extends proximally from distal shaft 176 along the exterior of proximal shaft 170. The catheter 160 includes proximal perfusion ports 197 through the wall of guide wire lumen proximal extension 195 and distal perfusion ports 196. Thus, during treatment, a guide wire extending through the guide wire lumen can be pulled back proximally to a point proximal of the proximal perfusion ports 197. This provides a perfusion pathway between the proximal ports 197 and distal ports 196, and accompanying blood flow during prolonged treatment.

Figure 13:
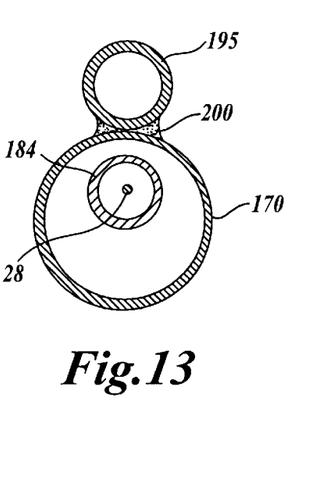
FIG. 13 is a cross section of the proximal shaft portion of the catheter of FIG. 10 at line 13—13.

FIG. 13 depicts a cross section of the catheter in FIG. 10 at line 13—13. The proximal guide wire extension 195 is depicted affixed to the outside diameter of proximal tube 170 via an adhesive bond 200. FIG. 13 also depicts core wire 28 extending within the inner tube 184.

Figure 14:
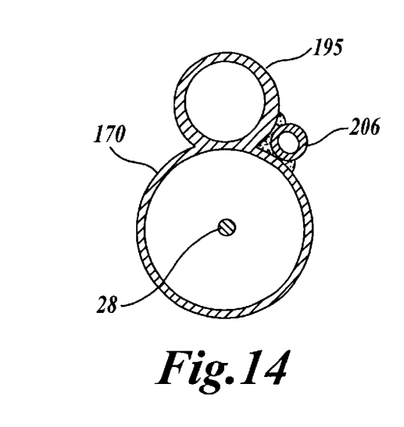
FIG. 14 is a cross section of an alternative proximal shaft portion similar to that of FIG. 13 incorporating a dual lumen extrusion for the proximal shaft.
Figure 15:
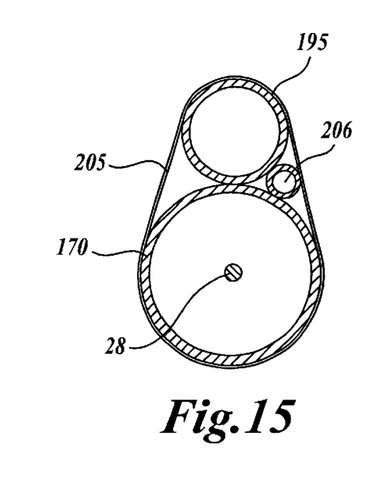
FIG. 15 is a cross section of an alternative proximal shaft portion similar to FIG. 13 which depicts the use of multiple separate tubular shafts which are bundled to form the proximal shaft portion.

FIGS. 14 and 15 depict alternative designs for the proximal portion of the catheter 160 with FIG. 14 incorporating a dual lumen proximal tubular member 170, and the catheter of FIG. 15 incorporating multiple tubular members in side-to-side relation bundled in a shrink wrap 205. The cross sections of FIGS. 14 and 15 are taken at line 13—13 of FIG. 10. The core wire 28 is depicted in both alternative embodiments within proximal tubular member 170. A separate inflation tubular member 206, having a lumen therethrough extends exterior to the proximal tubular member 170. The proximal guide wire extension 195 is an integral part of proximal tubular member 170 in FIG. 14, while in FIG. 15, the extension 195 is held to the exterior surface of the proximal tube 170 via the shrink wrap 205.

Numerous characteristics and advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A radiation source for inhibiting restenosis comprising:
   a tube, said tube having a lumen and a distal region, said distal region being radioactive, wherein said lumen is adapted to receive a core wire, said tube being slidable over the core wire, and wherein said tube has an outer surface adapted to slide within a balloon catheter.

2. A radiation source as recited in claim 1 wherein said tube is formed of metal.

3. A radiation source as recited in claim 1 wherein said tube has tube walls and said tube distal radioactive region includes radioactive material incorporated in said tube walls.

4. A radiation source as recited in claim 1 wherein said tube has a surf ace and said tube distal radioactive region includes radioactive material secured to said distal region surface.

5. A radiation source as recited in claim 1 wherein said tube has an exterior surface and said tube distal radioactive region includes radioactive wire wound about said distal region exterior surface.

6. A radiation source as recited in claim 1 wherein said tube is formed of metal and said tube distal radioactive region is formed of radioactive metal.

7. A radiation source as recited in claim 1 wherein said tube has a tube wall and a longitudinal slit through said tube wall, such that the guide wire is slidable through said longitudinal slit.

8. A radiation source as recited in claim 7 wherein said slit does not extend through at least a portion of said tube distal region.

9. A radiation source as recited in claim 1 wherein said tube distal region has a proximal guide wire port.

10. A radiation source as recited in claim 1 further comprising a shaft having a distal region, wherein said tube is disposed on said shaft distal region.

11. A catheter system for inhibiting restenosis comprising:
    an elongate tubular shaft having a lumen, a proximal region and a distal region;
    an inflatable balloon disposed about said shaft distal region, said balloon having a distal region, said balloon defining a balloon interior and exterior, said balloon interior being sealed with respect to fluid communication with said balloon exterior;
    a radiation source guide wire extending through said shaft lumen and through said balloon to said balloon distal region, said radiation source guide wire being operably attached to said balloon distal region; and
    an elongate radiation delivery tube, said delivery tube having a lumen to receive said radiation source guide wire and a distal region, said delivery tube distal region being radioactive, said delivery tube being slidable over said radiation source guide wire,
    such that said balloon is inflatable by infusing said tubular shaft lumen with inflation fluid,
    such that said radiation delivery tube is advancable over said radiation source guide wire, within said tubular shaft lumen, and into said balloon interior.

12. A catheter system as recited in claim 11 wherein said balloon includes a plurality of lobes.

13. A catheter system as recited in claim 11 wherein said balloon includes a plurality of tubular balloon segments disposed transversely about said radiation source guide wire.

14. A catheter system as recited in claim 11 wherein said radiation source is $Ru/Re_{106}$.

15. A catheter system as recited in claim 11 wherein said radiation delivery tube is formed from Nitinol.

16. A catheter system as recited in claim 11 wherein said radiation delivery tube is a polymeric tube formed from polyethylene.

17. A catheter system for inhibiting restenosis comprising:
    an elongate outer tube having a lumen, a proximal region and a distal region;
    an inflatable balloon disposed proximate said outer tube distal region, said balloon defining a balloon, interior and exterior, said balloon interior being sealed with respect to fluid communication with said balloon exterior;
    an elongate inner tube having a lumen, a proximal port, a distal region, and a closed distal end, said inner tube being disposed within said outer tube, said inner tube distal region being disposed inside said balloon;
    an inflation lumen defined between said inner and outer tubes, said inflation lumen being in fluid communication with said-balloon interior;
    a radiation source guide wire extending through said inner tube lumen and being fixed in said inner tube distal region; and
    an elongate radiation delivery tube, said delivery tube having a lumen to receive said radiation source guide wire and a distal region, said delivery tube distal region being radioactive, said delivery tube being slidable over said radiation source guide wire,
    such that said balloon is inflatable by infusing said inflation lumen with inflation fluid,
    such that said radiation delivery tube is advancable over said radiation source guide wire, within said inner tube lumen, and into said balloon interior.

18. A catheter system for inhibiting restenosis comprising:
    an elongate tubular shaft having a lumen, a proximal region and a distal region;
    an inflatable balloon disposed proximate said shaft distal region, said balloon having a distal region, said balloon defining a balloon interior and exterior, said balloon interior being sealed with respect to fluid communication with said balloon exterior;
    a radiation source guide wire extending through said shaft lumen and through said balloon, said radiation source guide wire being operably attached to said balloon distal region; and
    an elongate radiation delivery tube, said delivery tube having a lumen to receive said radiation source guide wire and a distal region, said delivery tube distal region being radioactive, said delivery tube being slidable over said radiation source guide wire,
    such that said balloon is inflatable by infusing said tubular shaft lumen with inflation fluid,
    such that said radiation delivery tube is advancable over said radiation source guide wire, within said tubular shaft lumen, and into said balloon interior.

19. A method for inhibiting restenosis comprising:
    providing a radiation delivery catheter including an elongate tubular shaft having a lumen, a proximal region and a distal region,
    an inflatable balloon disposed proximate said shaft distal region, said balloon defining a balloon interior and exterior, said balloon interior being sealed with respect to fluid communication with said balloon exterior, a radiation source guide wire extending through said shaft lumen and through said balloon to said balloon distal region, said radiation source guide wire being operably attached to said balloon distal region;

providing an elongate radiation delivery tube, said delivery tube having a lumen and a distal region, said delivery tube distal region being radioactive, said delivery tube being slidable over said radiation source guide wire, such that said balloon can be inflated by infusing said tubular shaft lumen with inflation fluid, such that said radiation delivery tube is advancable over said radiation source guide wire, within said tubular shaft lumen, into said balloon interior;

inserting said catheter distal region into the vascular system of a patient;

advancing said catheter distal region to a site to be treated;

inserting said radiation source guide wire into said. radiation delivery tube lumen;

advancing said radiation delivery tube over said radiation. source guide wire and within said tubular shaft lumen;

further advancing said radiation delivery tube within said balloon interior;

inflating said balloon;

exposing said treatment site to radiation;

deflating said balloon; and retracting said catheter and radiation delivery tube from said patient.

20. A method for inhibiting restenosis as recited in claim 19 further comprising the steps:

providing a radiation shielding vault having a channel therethrough;

housing said radiation delivery tube distal region in said vault channel prior to use; and advancing said radiation delivery tube distal region into said catheter lumen.

* * * * *